| United States Patent [19] | [11] | 4,431,120 |
|---|---|---|
| Burger | [45] | Feb. 14, 1984 |

[54] PACKAGING SYSTEM

[75] Inventor: Norman D. Burger, Culver City, Calif.

[73] Assignee: Nicholas A. Mardesich, Inglewood, Calif. ; a part interest

[21] Appl. No.: 193,353

[22] Filed: Oct. 2, 1980

Related U.S. Application Data

[62] Division of Ser. No. 789,639, Apr. 28, 1977, abandoned.

[51] Int. Cl.$^3$ ............................................. B65D 83/14
[52] U.S. Cl. ................................ 222/192; 222/402.18; 252/306
[58] Field of Search ...................... 252/305, 306, 316; 222/192, 402.18, 399

[56] References Cited

U.S. PATENT DOCUMENTS

| 3,081,223 | 3/1963 | Gunning | 167/39 |
|---|---|---|---|
| 3,122,284 | 2/1964 | Miles | 222/399 |
| 3,393,155 | 7/1968 | Schutte et al. | 252/2 X |
| 3,858,764 | 1/1975 | Watson | 222/399 |
| 3,964,649 | 2/1976 | Alexander | 222/399 |
| 3,974,945 | 8/1976 | Burger | 222/192 |
| 4,110,427 | 8/1978 | Kalat | 252/305 X |

*Primary Examiner*—David A. Scherbel

*Attorney, Agent, or Firm*—Beehler, Pavitt, Siegemund, Jagger & Martella

[57] ABSTRACT

An aerosol dispensing system includes a container having a valve-controlled opening for dispensing the container contents, which include hydrocarbon-adsorbent solids such as silica, hydrocarbon propellant adsorbed on such solids, and a weight ratio of hydrocarbon propellant to adsorbent solids ranging up to about 65 parts by weight of the contents, and a liquid composition that may include water, organic oils, alcohols, dispersed and dissolved metals, and metal salts. Water-encapsulating silica permits use of water in aerosol compositions, but prevents mixing of water with other substances in the composition until the composition is dispensed as an aerosol. Aerosol systems including containers with a valve-controlled opening and a valve for dispensing the container contents benefit from the addition of a capillary dip tube extending from the valve into the container contents where the contents are highly viscous. The capillary dip tube increases the velocity of the contents, and keeps them cohesive during movement through the tube. Aerosol system containers having a valve-controlled opening and a vapor tap valve for dispensing the container contents permit the aerosol dispensing of flammable compositions at controlled rates with acceptable flame extensions by dispersing vapor in the product emerging from the valve opening.

21 Claims, No Drawings

PACKAGING SYSTEM

This is a division of application Ser. No. 789,639, filed Apr. 28, 1977, which is a continuation-in-part of U.S. Ser. No. 728,779, filed Oct. 1, 1976, entitled AEROSOL DISPENSING SYSTEM, by Norman D. Burger both now abandoned.

This invention relates to an aerosol dispensing system that avoids the use of halogenated hydrocarbon propellants, and permits the dispensing of compositions having a wide range of viscosities with inexpensive propellants from conventional containers. The invention also relates to non-corrosive aerosol compositions for use in corrodible aerosol containers. Further, the invention relates to systems for increasing the flow rate of aerosol compositions from conventional aerosol containers by using a capillary dip tube. Still further, the invention relates to systems for dispensing flammable aerosols from conventional containers using valve-controlled openings to disperse vapor into the dispensed product.

Aerosol dispensing systems of many kinds are well known and widely utilized. Most of the known aerosol propellant systems rely upon halogenated hydrocarbons, principally fluorocarbons, as propellants, but these propellants are now known to be degrading the earth's ozone layer. Moreover, these propellants are becoming increasingly expensive, and most aerosol systems that use them require high concentrations of propellant, and low concentrations of other ingredients, including active ingredients, and are therefore quite wasteful.

This invention provides aerosol systems that can propel compositions having a wide range of viscosities with relatively inexpensive propellants, and particularly hydrocarbon propellants, that do not damage the ozone layer of the earth, and that are safe and nonflammable in this system.

More specifically, this invention provides an aerosol system for use with conventional containers having a valve-controlled opening and a conventional valve for dispensing the contents of the container. This system also permits the dispensing of aqueous compositions from containers even where the aqueous system is highly acid. Importantly, the system permits the use of hydrocarbon propellants in relatively large quantities with virtually no flammability, as measured by standard industry tests.

The new system comprises a wet composition that may have a viscosity in the range of about 0.5 centistokes to about 10,000 centistokes, or of 50 seconds or even longer measured with the No. 3 Zahn cup, and may have a pH ranging from highly acid, e.g., 1-2, to highly alkaline, e.g., 14-15. The composition comprises at least three categories of constituents:

(a) Hydrocarbon-adsorbent solids such as high surface area amorphous silicas, in an amount sufficient to adsorb substantially all of the hydrocarbon propellant, optionally including lesser amounts of water-encapsulating solids;

(b) At least one hydrocarbon propellant, meaning a propellant that is made of carbon and hydrogen atoms only, substantially all of which is adsorbed by the hydrocarbon-adsorbent solids, and in amounts comprising about 6 to about 11 times the weight of the hydrocarbon-adsorbent solids; and (c) A liquid composition that is present in an amount sufficient to make the composition wet, and which may contain water. Where water forms part of the liquid composition, the weight ratio of water to water-encapsulating solids must be in the range of about three to one to about five to one. The balance of the liquid composition may include such substances as organic oils and alcohols, dissolved or suspended metals and metal salts, and chlorinated solvents.

Optionally, the composition may include:

(d) Particulate solids other than hydrocarbon adsorbent solids that have a mesh size in a range that permits them to pass through the openings of valves used in aerosol systems.

The new aerosol system is ideally suited for dispensing deodorants and anti-perspirants of widely varying viscosities and widely varying solids and liquid contents. In this system, these compositions may have viscosities varying from about 0.5 centistokes to about 10,000 centistokes, which means that the compositions may vary from nearly liquid to virtually solid compositions. The new compositions are also adaptable to the dispensing of materials such as insecticides, hairsprays, disinfectants and other space sprays, water- and oil-based paints, and many other food and non-food materials.

The first category of ingredients included in the new composition, the hydrocarbon-adsorbent silicas, may be present in amounts of from about 2% by weight to about 8% by weight of the overall composition, preferably about 3.5% to about 4.5% by weight, depending upon the nature and quantity of the hydrocarbon-adsorbent solids, and of the other ingredients, especially the propellant, to be dispensed, the desired dispensing rate, and the presence or absence of water in the composition.

The hydrocarbon-adsorbent solids include, but are not limited to, amorphous silicas and silicates, preferably the amorphous silicas having high surface area, mean ultimate particle size in the order of about 5 to about 20 thousandths of a micron, surface areas greater than about 100 square meters per gram, and densities in the range of at least about 2 pounds per cubic foot. Preferably, such silicas and silicates have a pH that is less than about 7 but pH's above 7 are acceptable. Examples of such hydrocargon-adsorbent solids are fumed amorphous silicas having a hydrophobic surface such as Tullanox 500 made by Tulco, Inc., of North Billerica, Mass., which has a specific gravity of 2.2, a refractive index of 1.76, a bulk density of 3 pounds per cubic foot, and a surface area of 325 square meters per gram; precipitated amorphous silicas having hydrophobic surfaces such as QUSO ® silicas WR50 and WR82, made by Philadelphia Quartz Company, and having surface area of 130 and 120 square meters per gram, respectively, pH of 10.4 and 11.5, respectively, bulk density of 10 pounds per cubic foot and 10 pounds per cubic foot, respectively, and aggregate particle size of 1.8 µm and 2.3 µm, respectively; precipitated amorphous silicas having a hydrophilic surface, such as QUSO ® silicas G30 and G32, having ultimate particle size of 14 nm (both), surface area of 300 square meters per gram (both), pH of 8.5 (both), bulk densities of 10 and 4 pounds per cubic foot, respectively, refractive index of 1.45 (both), and specific gravity of 2.1 (both); and silicates such as Philadelphia Quartz Company's magnesium silicate Britesorb ®. The preferred hydrocarbon-adsorbent solids are the high surface area fumed amorphous silicas having hydrophilic surfaces made by Cabot Corporation, and called Cab-O-Sil, especially Cab-O-Sils M-5 and EH-5. These silicas have surface areas of two hundred plus or minus twenty-five square meters per gram and three hundred ninety plus or minus forty square meters per gram, respectively, and densities of about 2.3 pounds per cubic foot. They have a pH, measured as a four percent concentration in water, in the range 3.5 to 4.2. They have a nominal particle size in microns of 0.014 and 0.007, respectively. Both have a bulking value of about 5.5 gallons per hundred pounds, a specific gravity of 2.2, are white in color, and have a silica content greater than 99.8% and a refractive index of about 1.46.

Where the composition nominally contains no water, water-encapsulating solids need not be present, but preferably small amounts, such as for example, up to about 0.2%, will be present to trap moisture in the composition. Where water is present, the water-encapsulating solids must be present in a weight ratio of water to water-encapsulating solids in the range of about 3 to 1, to about 5 to 1, preferably about 4 to 1. The preferred water-encapsulating solids are water-encapsulating silicas. More preferably, the water-encapsulating solids are hydrophobic amorphous silicas such as Tullanox 500, but others such as QUSO ® WR50 and WR82 may also be used.

The new composition permits the use of hydrocarbon propellants without any other kind of propellant besides the hydrocarbon adsorbent solids. Besides the lower cost of these materials than the halogenated hydrocarbons presently used in aerosols, these propellants are nondeleterious to the environment, and are nonflammable in the new system as measured by the CSMA (Chemical Specialties Manufacturers Association) standard flame extension test and open and closed drum tests. These propellants include such hydrocarbons as methane, ethane, propane, n-butane, isobutane, isopentane and pentane. Substantially all of the propellant is adsorbed by the hydrocarbon adsorbent solids of the composition, and the propellant is present in a weight ratio of propellant to hydrocarbon adsorbent solids in the range of about 6 to 1 to about 11 to 1, preferably about 10 to 1. Thus, the amount of propellant may vary from as little as about 10% by weight of the overall composition to as much as about 90% by weight, preferably about 20% to about 50% by weight.

In some cases, the propellant may constitute more than 11 times the weight of the hydrocarbon adsorbent solids, such as where some unadsorbed propellant is desired to insure an adequate supply of propellant to the vapor tap in the vapor tap valve that is used with these compositions. This additional hydrocarbon propellant may raise the ratio of propellant to hydrocarbon adsorbent solids to as high as about 15 to 1.

Although the hydrocarbon propellants may be used alone in the new composition, halogenated hydrocarbons may also be present, if desired. Carbon dioxide, nitrous oxide and other relatively non-liquifiable compressed gases may be present as well, if desired.

Advantageously, this new system permits incorporation of a wide range of percentages by weight of particulate solids, provided the solids have a mesh size that permits their passage through the opening in the stem of valves normally used in aerosol systems. Thus, for example, the mesh size of the solids should not be greater than Number 60 (U.S. Standard Seive), preferably not greater than 140, and more preferably not greater than about 200. Solids commonly used as fillers and diluents for antiperspirant sprays, particularly those containing aluminum chlorohydrate, include talcs such as Pfizer, Inc.'s Talcron MP50-30 and corn starches such as Vulca-90 and Dri-Flo made by National Starch and Chemical Corporation. Other solids such as sodium carbonate, sodium bicarbonate, and other light metals and light metal salts, e.g., zirconyl hydroxychloride also may be used. One or more of these kinds of particulate solids may be present in the composition, and these solids may constitute up to about 65% by weight of the composition, depending on the maker's desire.

It is essential that the hydrocarbon-adsorbent solids-containing composition used in the aerosol system of this invention be wet, though the viscosity of the composition may vary widely. The composition may include no water at all, but advantageously permits the presence of up to about 25% water on the weight of the composition, preferably not more than about 15% by weight of the composition. Where water is present, water-encapsulating solids must be present in a weight ratio of water to water-encapsulating solids in the range of about 3 to 1 to about 5 to 1, preferably about 4 to 1. The balance of the liquid may be such non-aqueous substances as lower alkyl alcohols, especially ethyl alcohol, organic oils and emollients, such as isopropyl myristate, isopropyl palmitate, and the like. The liquid may also include dissolved solids, suspended solids, or both, in amounts ranging from trace quantities up to about 65% by weight of the overall composition. In anti-perspirant compositions that include astringents such as aluminum chloride and aluminum chlorohydrate, the emollient may constitute up to about 50% of the composition.

The compositions of this invention are particularly adapted to the aerosol dispensing of deodorants and anti-perspirants. Modern anti-perspirants commonly include aluminum chlorohydrate and aluminum chloride as active ingredients, and are combined in aerosols with propellants and with inert powders, oily emollients, or some mixture of the two. Consumer preferences dictate a wide range of viscosities and textures in anti-perspirant sprays, ranging from oily to dry and powdery. The system of this invention may be adapted to any anti-perspirant in this range of textures. Thus, for example, where a dry powdery spray is desired, the particulate solids, silica and propellant will constitute a larger percentage of the composition than does the liquid composition.

The use of water-encapsulating solids in this system permits the presence of water in amounts ranging up to about 25%, but preferably ranging up to not higher than about 15%, by weight of the container composition. Aluminum chlorohydrate (ACH) and aluminum chloride (AC) are much more effective anti-perspirants where combined with water than where no water is present in the anti-perspirant composition. The water-encapsulating solids encapsulate water droplets in the container and insulate the water from other materials in the container, and from the inner surfaces of the container. This encapsulation permits the use of materials in the system which would be chemically active if they combined with water. Insulated from water, such materials are, and remain relatively inert in the container. Upon dispensing through the container valve, however, the shearing action of the spray valve breaks the encapsulation, and frees the water to mix with other constituents dispensed from the container.

Water-encapsulating solids may be used in a wide variety of aerosol compositions besides the solid state aerosols of this invention. Water-encapsulating solids isolate water or water-active substances blended with water from other substances in such compositions. This isolation prevents reaction of water with other substances that would otherwise occur in containers for such compositions. Thus, if the aerosol container includes water-active substances that become corrosive when mixed with water and attack the surfaces of such containers, adding water-encapsulating solids will prevent this. Water-encapsulating solids include, but are not limited to, those amorphous silicas having hydrophobic surfaces, including Tullanox 500 and QUSO ® silicas WR50 and RW82. Where Tullanox 500 is the water-encapsulating solid, the ratio of water or of water plus dissolved water-active solids to the water-encapsulating silicas may be in the range of about 8 to 1 to about 3 to 1.

The water-encapsulating solids are best dispersed with the water, avoiding shearing forces which interfere with the encapsulating mechanism. In aerosol anti-perspirant compositions, water-encapsulating solids may be used to isolate water from metal salts such as ACH and AC, or to isolate the mixture of water and such solids from the rest of the composition. As a result, the water/metal salt blend is prevented from attacking the container for the composition, yet the encapsulation is readily broken by the shearing forces exerted on the composition when dispensed from the valve controlling outlet from the container.

The new compositions may be formulated by blending the hydrocarbon adsorbent silicas with the other particulate solids in proportions appropriate for making the desired container composition. The liquid composition is formulated separately, then blended with the solids blend. The combined liquids/solids blend is placed into containers, which are pressurized with the desired quantity of hydrocarbon propellant. Alternatively, the hydrocarbon adsorbent solids may be blended directly with propellant before filling the container with the blend.

Where water is to be part of the composition, the water is preferably added alone to the blend of solids before any other liquid such as an oil is added. The water should be dispersed in the solids at low shear until the water-encapsulating solids have encapsulated the water. Surfactants, if any, should be added to the oil phase, and should constitute not more than about 0.9% of the container composition.

Overall, the new compositions may include about 2% to about 70–75% solids, about 12% to about 55% hydrocarbon propellant, and 0% to about 45% liquids, all based on the weight of the container composition. The viscosity of the compositions may range from about 0.5 centistokes to about 10,000 centistokes, more commonly up to about 5,000–6,000 centistokes, and may therefore accommodate the dispensing of many different kinds of products at many different rates of dispensing, and all of these compositions may be dispensed with conventionally made pressure-tight containers, valves and dip tubes.

It should be apparent that the aerosol system of this invention is radically different from known aerosol formulations, which generally require a low viscosity liquid concentrate, typically slurried or thinned with liquid propellant. Such prior art systems have viscosities anywhere from 0.5 to 250 centistokes. At these viscosities, hydrocarbons such as butane and propane cannot be the propellant in previously disclosed aerosol systems because flammability would be extremely high and hazardous, unless flame retardants such as water are present in substantial quantities.

Accordingly, conventional aerosol formulations cannot tolerate more than about 15% by weight of a hydrocarbon propellant without producing excessive flammability. Flammability has been previously reduced in such formulations by adding harsh solvents such as methylene chloride. Unfortunately, these solvents are undesirable in many formulations particularly anti-perspirant formulations because they cause skin irritation and some inhalation toxicity.

The invention, by contrast, provides a solid state propellant system which not only permits, but takes advantage of higher viscosity formulations to reduce the flammability of hydrocarbon propellants to a safe level. No solvents or thinning agents or flame retardants need be utilized in this system, yet the system produces desirable delivery rates of dispensed product with virtually no flammability.

This new system achieves these highly desirable results by combining appropriate size capillary dip tubes, valve stems, and vapor taps with a unique propellant system that may be substantially all hydrocarbons adsorbed by certain hydrocarbon adsorbent solids to achieve a system that can deliver as little product as 50 to 750 milligrams per second from an aerosol dispenser, and as much as 1.5 to 2 or even more grams per second from the same equipment.

In particular, the vapor tap valve permits the codispensing at a controlled rate of product and propellant together with a considerable quantity of vaporized hydrocarbon propellant to produce a spray that is non-flammable when measured by standard industry tests. The vapor phase of such propellants is considerably less flammable than the liquid phase of the same propellants. Thus, for example, 200 mg/second of vapor phase hydrocarbon propellant dispensed as an aerosol is virtually non-flammable; whereas, 200 mg/sec of the liquid phase of the same dispensed propellant is highly flammable. Preferably, the vapor tap orifice diameter is in the range of about 0.010 to about 0.025 inch, and will ordinarily be no larger in diameter than the diameter of the stem orifice. In these valves, the stem orifice preferably will be in the range of about 0.010 to about 0.030 inch.

The capillary dip tubes used in this system permit control of the rate of product and propellant dispensing. To that end, the inside diameter of the dip tube becomes smaller as the viscosity of the aerosol system's contents increases to produce a sufficient velocity of the contents up the dip tube to the valve, and to produce an acceptable spray from the valve. As the viscosity decreases, the inside diameter of the capillary dip tube increases to reduce the velocity of the contents of the dip tube to the valve, and to produce an acceptable spray from the valve. The preferred vapor tap valve will be joined to a capillary dip tube having an inner diameter in the range of about 0.030 to about 0.040 inch.

Capillary dip tubes and vapor tap valves may be advantageously used to dispense aerosol compositions other than the solid state compositions of this invention from conventional aersol containers. Thus, if the compositions include at least one flammable constituent that would ordinarily produce an unacceptable flame extension when dispensed, a conventional aerosol container may be fitted with a vapor tap valve to disperse larger quantities of relatively non-flammable vapor into the aerosol spray. This vapor tends to reduce the flammability of the spray, and to shorten the flame extension of the dispensed product. Optionally, such a container may also be fitted with a capillary dip tube which tends to accelerate the container contents toward the valve opening, keeps the container composition cohesive as it moves through the capillary dip tube, and thus minimizes fluttering and sputtering of the aerosol spray as dispensed. Moreover, the capillary dip tube also tends to reduce the quantity of products delivered per unit of time, thus helping to control further the flame extension of the dispensed aerosol composition.

Even where the aerosol composition does not contain a flammable constituent, the capillary dip tube may be used to increase the velocity of product delivered to the valve opening, particularly where the aerosol composition has a high viscosity, such as 500 centistokes or more.

The flammable constituent in the composition may be the propellant, such as a hydrocarbon propellant, another constitutent, such as alcohols and silicones, or both. The capillary dip tube, if any, should have an internal diameter in the range of about 0.020 inch to about 0.050 inch. Larger diameter dip tubes preclude accelerating highly viscous aerosol compositions therethrough because cavitation occurs in the dip tube. The vapor tap valve should have a vapor tap diameter in the range of about 0.010 to about 0.030 inch, and a stem orifice diameter in the range of about 0.010 to about 0.040 inch. The valve may have one or more than one stem orifice opening, but each of these openings will commonly have a diameter in this range.

The relationship of vapor tap diameter to stem orifice diameter and to capillary dip tube internal diameter may vary depending on the degree of flammability of the aerosol composition. Thus, the vapor tap diameter may be substantially larger than the stem orifice diameter where the aerosol composition is very highly flammable. For example, with aerosol hair spray compositions containing larger proportions of such highly flammable constituents as alcohols, the capillary dip tube internal diameter may be 0.030 inch, the vapor tap diameter, in the range 0.015 to 0.025 inch, and the stem orifice diameter in the range 0.010 to 0.016 inch. With the stem orifice diameter substantially smaller than the vapor tap diameter, the aerosol composition as dispensed will contain a large quantity of dispersed vapor, which tends to reduce the flammability and flame extension of the dispensed composition.

The new propellant system of this invention is not limited to use in aerosol spray systems. The propellant system of the invention may also be adapted for use in dispensing such high viscosity products as creams, lotion and gels without foaming or otherwise disturbing the physical state of such products. Because such products are dispensed are relatively viscous liquids, smaller quantities of hydrocarbon propellant, preferably in the range of about 1 or 2% to about 4 or 5%, more preferably about 3%, by weight of the composition, will be sufficient to dispense such high viscosity products with little or no foaming in the dispensed product.

As with the use of the new propellant system in aerosol sprays, the propellent principally comprises at least one hydrocarbon propellant, meaning a propellant that is made of carbon and hydrogen atoms only, substantially all of which is adsorbed by the hydrogen-adsorbent solids, in amounts comprising about 6 to about 11 times the weight of the hydrocarbon-adsorbent solids. Unlike the application of this propellant system to aerosol sprays, however, water-encapsulating solids may, but need not be used. The kinds of hydrocarbon-adsorbent solids and hydrocarbon propellants may be the same as those used in the aerosol spray systems of this invention, and are described in detail above. Further, the weight ratio of hydrocarbon propellant to hydrocarbon-adsorbent solid must be in the range of about 6 to 1 to about 11 to 1, preferably about 10 to 1.

High viscosity products such as creams, lotions and gels may be dispensed from conventional aerosol propellant containers equipped with capillary dip tubes having an internal diameter in the range of about 0.030 to about 0.040 inch, and from standard dispensing valves that may have a stem orifice diameter in the range of about 0.010 to about 0.030 inch. Such valves have no vapor tap.

In summary, then, where the propellant system of this invention is adapted for use in dispensing such high viscosity products as creams, lotions and gels, the dispensing system will be made up of a container equipped with a conventional valve and having a capillary dip tube extending from the valve into the container contents. The contents will comprise from about 1 to about 5% hydrocarbon propellant, and from 1/6th to about 1/11th, more preferably about 1/10th of the hydrocarbon propellant by weight of hydrocarbon adsorbent solids, based on the weight of the overall composition. The balance of the container contents will be made up of one or more high viscosity products which may or may not contain some particulate solids, some dissolved solids, or both. The viscosity of these composition contents may be up to about 8,000 centistokes.

The following examples illustrate the application of the new aerosol system to the formulation of anti-perspirant aerosol compositions. Unless otherwise indicated, all percentages are by weight based on the weight of the overall composition inside the container, and therefore exclusive of the weight of the container, valve and dip tubes.

EXAMPLE I

Following the method prescribed above, the following composition was formulated:

| Ingredient | Percentage by weight |
| --- | --- |
| Cab-O-Sil EH-5 | 4 |
| Cornstarch (Vulca 90) | 15 |
| Aluminum Chlorohydrate | 17 |
| Isopropyl myristate | 31.5 |
| Propellant A46 (1) | 32.5 |
| | 100.0 |

(1) Blend of propane, isobutane and n-butane, having a vapor pressure of about 46 pounds per square inch gauge.

This composition has a viscosity of about 2,000 centistokes, and dispenses 350 milligrams per second of ingredients from a metal container fitted with a vapor tap valve that has a stem valve diameter of 0.014 inch, a vapor tap diameter of 0.013 inch, and having a capillary dip tube with an inner diameter of 0.030 inch.

This aerosol composition proved substantially non-flammable in the CSMA test, producing a 0 to 2 inch flame extension measured at six inches from the terminal orifice of the actuator. The composition also passed successfully the open and closed drum tests.

This aerosol composition dispensed more readily from a similar container fitted with a valve having a stem orifice diameter in the range 0.016 to 0.020 inch and a vapor tap diameter of about 0.014 inch.

EXAMPLE II

Following the method prescribed above, the following composition was formulated:

| Ingredient | Percentage by weight |
| --- | --- |
| Cab-O-Sil EH-5 | 2.3 |
| Tullanox T500 | 1.3 |
| Cornstarch (Vulca 90) | 30.8 |
| Aluminum Chlorhydrate | 10.0 |
| Isopropyl myristate | 20.0 |
| Propellant A46 (1) | 35.6 |
| | 100.0 |

(1) Blend of propane, isobutane and n-butane, having a vapor pressure of about 46 pounds per square inch gauge.

This anti-perspirant composition dispenses approximately 350 milligrams per second of ingredients from a metal container fitted with a vapor tap valve with a stem valve diameter of 0.014 inch, and a vapor tap diameter of 0.013 inch, and with a capillary dip tube with an inner diameter of 0.030 inch.

This aerosol composition proved substantially nonflammable in the CSMA test, producing a 0 to 2 inch flame extension measured six inches from the terminal orifice of the actuator. The composition also passed successfully the open and closed drum tests.

This aerosol composition dispensed more readily from a similar container fitted with a valve having a stem orifice diameter in the range 0.016 to 0.020 inch and a vapor tap diameter of about 0.014 inch.

EXAMPLE III

| Ingredient | Percentage by Weight |
| --- | --- |
| Cab-O-Sil EH-5 | 3.6 |
| Tullanox T500 | 1.3 |
| Cornstarch (Dri-Flo) | 29.5 |
| Aluminum Chlorhydrate | 10.0 |
| Isopropyl Myristate | 14.8 |
| Propellant A46 (1) | 35.6 |
| Water | 5.2 |
| | 100.0 |

(1) Blend of propane, isobutane and n-butane, having a vapor pressure of about 46 pounds per square inch gauge.

This anti-perspirant composition dispenses approximately 350 milligrams per second of ingredients from a pressure-tight metallic container fitted with a vapor tap valve with a stem valve diameter of 0.014 inch, and a vapor tap diameter of 0.013 inch, and with a capillary dip tube with an inner diameter of 0.030 inch.

This aerosol composition proved substantially nonflammable in the CSMA test, producing 0 to 2 inch flame extension measured six inches from the terminal orifice of the actuator. The composition also passed successfully the open and closed drum tests.

This aerosol composition dispensed more readily from a similar container fitted with a valve having a stem orifice diameter in the range 0.016 to 0.020 inch and a vapor tap diameter of about 0.014 inch.

What is claimed is:
1. An aerosol system comprising:
   a container having a valve-controlled opening, a valve for dispensing the container contents, and a dip tube extending from said valve into said container contents; and
   a composition in said container comprising:
   (a) at least one hydrocarbon adsorbent solid and 0 to about 10% by weight of at least one water-encapsulating solid;
   (b) at least one hydrocarbon propellant, substantially all of said hydrocarbon propellant being adsorbed by the hydrocarbon adsorbent solid, the ratio of said hydrocarbon propellant to said hydrocarbon adsorbent solid being in the range of about 6 to 1 to about 11 to 1; and
   (c) a liquid composition present in sufficient amount to make said composition wet that includes 0 to about 25% water, based on the weight of the container composition, the weight ratio of water to said water-encapsulating solid being in the range of about 3 to 1 to about 5 to 1.
2. The aerosol system of claim 1 wherein said composition also includes:
   (d) at least one particulate solid other than said hydrocarbon adsobent solid and water-encapsulating solid that has a mesh size in a range that permits passage through the openings of valves in aerosol systems.
3. The aerosol system of claim 2 wherein the composition comprises one hydrophilic surfaced amorphous silica and one hydrophobic amorphous silica.
4. The aerosol system of claim 3 wherein the composition comprises one hydrophilic surfaced amorphous silica and one hydrophobic amorphous silica.
5. The aerosol system of claim 1 wherein the composition comprises one hydrophilic surfaced amorphous silica and one hydrophobic amorphous silica.
6. The aerosol system of claim 5 wherein said hydrophilic surfaced amorphous silica is Cab-O-Sil EH-5 or Cab-O-Sil M5 and said hydrophobic amorphous silica is Tullanox 500.
7. The aerosol system of claim 1 wherein the container composition has a viscosity in the range of about 0.5 to about 10,000 centistokes.
8. The aerosol system of claim 1 wherein the particulate solids have a mesh size in the range of less than about 60 mesh to less than about 200 mesh, and are selected from the group consisting of talc, cornstarch, sodium bicarbonate, aluminum chloride, and aluminum chlorhydrate.
9. The aerosol system of claim 1 wherein said liquid composition comprises at least one member selected from the group consisting of water, lower alkyl alcohols, organic oils, aluminum chloride and aluminum chlorhydrate. from the group consisting of water, lower alkyl alcohols, organic oils, aluminum chloride and aluminum chlorhydrate.
10. The aerosol system of claim 1 wherein the valve is a vapor tap valve having a stem orifice with a diameter in the range of about 0.010 inch to about 0.030 inch, a vapor tap orifice diameter in the range of about 0.010 to about 0.025 inch, and said dip tube is a capillary dip tube having an inner diameter in the range of about 0.030 to about 0.040 inch.
11. The aerosol system of claim 1 wherein the hydrocarbon adsorbent solids are selected from amorphous silicas having hydrophilic surfaces, amorphous silicas having hydrophobic surfaces, and silicates.
12. The aerosol system of claim 1 wherein the water-encapsulating solids are amorphous hydrophobic silicas.
13. The aerosol system of claim 1 wherein the amorphous hydrophobic silicas are fumed.
14. An aerosol system comprising:

a container having a valve-controlled opening, a valve for dispensing the container contents, and a dip tube extending from said valve into said container contents; and a composition in said container comprising;
(a) at least one hydrocarbon adsorbent solid;
(b) at least one hydrocarbon propellant, substantially all of said hydrocarbon propellant being adsorbed by the hydrocarbon adsorbent solid, the ratio of said hydrocarbon propellant to said hydrocarbon adsorbent solid being in the range of about 6 to 1 to about 11 to 1; and
(c) at least one high viscosity product selected from the group consisting of creams, lotions and gels, said composition having a viscosity not greater than about 8,000 centistokes.

15. A pressurized aerosol container system including a composition comprising:
(a) at least one hydrocarbon adsorbent solid and 0 to about 10% by weight of at least one water-encapsulating solid;
(b) at least one hydrocarbon propellant, substantially all of said hydrocarbon propellant being adsorbed by the hydrocarbon adsorbent solid, the ratio of said hydrocarbon propellant to said hydrocarbon adsorbent solid being in the range of about 6 to 1 to about 11 to 1; and
(c) a liquid composition present in sufficient amount to make said composition wet that includes 0 to about 25% water, based on the weight of the composition, the weight ratio of water to said water-encapsulating solid being in the range of about 3 to 1 to about 5 to 1.

16. The system of claim 15 wherein said composition includes at least one amorphous silica having a hydrophilic surface and one hydrophobic amorphous silica, and substantially no water.

17. The system of claim 15 wherein said composition includes at least one amorphous silica having a hydrophilic surface and one hydrophobic amorphous silica, and including up to about 25% water by weight of the container composition.

18. The system of claim 15 wherein the hydrocarbon adsorbent solids are selected from amorphous silicas having hydrophilic surfaces, amorphous silicas having hydrophobic surfaces, and silicates.

19. The system of claim 15 wherein the water-encapsulating solids are amorphous hydrophobic silicas.

20. The system of claim 19 wherein the amorphous hydrophobic silicas are fumed.

21. A pressurized aerosol container system including a composition comprising;
(a) at least one hydrocarbon adsorbent solid;
(b) at least one hydrocarbon propellant, substantially all of said hydrocarbon propellant being adsorbed by the hydrocarbon adsorbent solid, the ratio of said hydrocarbon propellant to said hydrocarbon adsorbent solid being in the range of about 6 to 1 to about 11 to 1; and
(c) at least one high viscosity product selected from the group consisting of creams, lotions and gels, said composition having a viscosity not greater than about 8,000 centistokes.

* * * * *